(12) United States Patent
Barrett et al.

(10) Patent No.: US 10,226,049 B2
(45) Date of Patent: Mar. 12, 2019

(54) LARVICIDAL COMPOSITION

(71) Applicant: Granular Products Assets Pty Ltd, Orange, New South Wales (AU)

(72) Inventors: Graham Barrett, Orange (AU); Philip Pentland, Flemington (AU); Abhinetiri Kumari Maharaj, Greenvale (AU)

(73) Assignee: Granular Products Assets PTY LTD, Orange, New South Wales (AU)

( * ) Notice: Subject to any disclaimer, the term of this patent is extended or adjusted under 35 U.S.C. 154(b) by 322 days.

(21) Appl. No.: 15/114,622

(22) PCT Filed: Feb. 4, 2015

(86) PCT No.: PCT/AU2015/000059
§ 371 (c)(1),
(2) Date: Jul. 27, 2016

(87) PCT Pub. No.: WO2015/117188
PCT Pub. Date: Aug. 13, 2015

(65) Prior Publication Data
US 2016/0345584 A1    Dec. 1, 2016

(30) Foreign Application Priority Data

Feb. 4, 2014 (AU) ............................... 2014900319

(51) Int. Cl.
*A01N 63/00* (2006.01)
*A01N 25/28* (2006.01)
*A01N 63/02* (2006.01)

(52) U.S. Cl.
CPC .............. *A01N 63/00* (2013.01); *A01N 25/28* (2013.01); *A01N 63/02* (2013.01)

(58) Field of Classification Search
CPC ......... A01N 63/00; A01N 25/28; A01N 63/02
See application file for complete search history.

(56) References Cited

U.S. PATENT DOCUMENTS

| 3,271,243 | A | 9/1966 | Cords et al. |
| 4,166,112 | A | 8/1979 | Goldberg |
| 5,484,600 | A | 1/1996 | Sjogren |
| 2003/0064060 | A1 | 4/2003 | DeChant |
| 2004/0185079 | A1 | 9/2004 | Zomer |
| 2010/0143481 | A1* | 6/2010 | Shenoy ............... A61K 9/2077 424/489 |
| 2011/0306502 | A1 | 12/2011 | Shah et al. |

FOREIGN PATENT DOCUMENTS

| EP | 1306008 A1 | 5/2003 |
| WO | 1989/007605 A1 | 8/1989 |
| WO | 2007/034250 A1 | 3/2007 |

OTHER PUBLICATIONS

International Search Report and Written Opinion for corresponding Application No. PCT/AU2015/000059 (dated May 5, 2015).
International Preliminary Report on Patentability for corresponding Application No. PCT/AU2015/000059 (dated May 17, 2016).
Prasad et al., "Development of Water Dispersible Powder (WDP) Formulation of *Bacillus thuringiensis* var. kurstaki and Evaluation Against *Helicoverpa armigera* (Hubner)," Pesticide Res. J. 18(2):179-182 (2006).

* cited by examiner

*Primary Examiner* — Trevor Love
(74) *Attorney, Agent, or Firm* — LeClairRyan PLLC

(57) ABSTRACT

An insecticidal granular composition for broadcasting of the granular composition onto a body of water on which insects are to be controlled comprising: a granular carrier of size in range of from 1 to 4 mm; a composition absorbed into the granular carrier comprising a bacterially derived larvicidal active agent and a non-aqueous liquid having a density less than 1; wherein the insecticidal granular composition has an average individual granule density greater than 1 and is adapted to sink in the body of water.

15 Claims, No Drawings

LARVICIDAL COMPOSITION

This application is a national stage application under 35 U.S.C. § 371 of PCT Application No. PCT/AU2015/000059, filed Feb. 4, 2015, which claims the priority benefit of Australia Application No. 2014900319, filed Feb. 4, 2014.

TECHNICAL FIELD

The invention relates to an insecticidal granular composition and in particular to an insecticidal granular composition comprising a biological larvicide such as *Bacillus thuringiensis* (Bt) or *Bacillus sphaericus* (Bs), to a method of preparing such a composition and to the use of such a composition in control of insects.

BACKGROUND OF INVENTION

Larvicidal material, including material taken from *Bacillus thuringiensis* var. *Israelensis* (Btl) and material taken from Bs (*Bacillus sphaericus*) has been used to control insects such as mosquitoes by application of the material in the form of a spray or in the form of granules to bodies of shallow water that contain mosquito larvae. *Bacillus* materials can be added to water in a spray tank in the form of a wettable powder, or in the form of an emulsifiable concentrate (where the material is suspended in a water immiscible oil which includes surfactants that facilitates dispersion in water).

U.S. Pat. No. 3,271,243 (Cords and Fisher, 1963) discloses a stable concentrated bacterial insecticidal suspension. The bacteria, when cultivated in an appropriate aqueous nutrient media, form spores and also form crystallised proteins which are toxic to insects.

US 2004/0185079 (Zomer, filed 2002) refers to a method to control insects by broadcasting a sustained release pesticide granular composition comprising 5-60% of a larvicidal protein, 5-60% floating hollow particles coated with hydrophobic material, 1-25% water-soluble sunscreen pigment and 1-25% of insoluble fibrous matrix. Preferences are noted as follows: (i) a release period of about 30 days, (ii) flotation agent selected from perlite, vermiculite, industry by-products such as feather or peanut shell particles, cellulose by-products such as corn cob and cork-derived materials, (iii) flotation agents to be treated with hydrophobic material such as paraffin, hydrophobic silica, natural fats, oils, (iv) inclusion of larvae feeding stimulants such as fish meal, soy meal, yeast meal), (v) inclusion of 0.1-5% detergents such as alkylpolysaccharides or Tweens, (vi) use of humate as the sunscreen agent, (vii) use of insoluble fibrous matrix from industrial sludges.

The larvicide is most effective at the air-water interface. This generally means having granules that have a low granule density so the granules float to provide an effective concentration of larvicide at the air water interface. However granules with a low density also have low packing density, so that aerial application from aircraft such as helicopters or fixed wing aircraft is expensive due to the limited carrying capacity of aircraft.

SUMMARY OF INVENTION

We have found that effective insect control can be achieved using a high density granular composition comprising a granular carrier in which the larvicidal active and non-aqueous liquid of density less than 1 is absorbed.

Accordingly we provide an insecticidal granular composition for broadcasting of the granular composition on a body of water on which insects are to be controlled comprising:
a granular carrier of size in range of from 1 to 4 mm;
a composition absorbed into the granular carrier comprising a bacterially derived larvicidal active agent and a non-aqueous liquid having a density less than 1;
wherein the insecticidal granular composition has an average individual granule density greater than 1 and is adapted to sink in the body of water.

There is further provided a process for preparation of an insecticidal granular composition for broadcasting on a body of water, comprising:
providing a granular carrier of size in the range of form 1 to 4 mm; and
mixing the carrier with a suspension of larvicidal active in a non-aqueous liquid to absorb the suspension into the granules;
wherein the non-aqueous liquid has a density less than 1 and the insecticidal granular composition has an average individual granule density greater than 1 and is adapted to sink in the body of water.

There is also provided a method for the control of insects on a body of water, comprising applying to the body of water the above described insecticidal granular composition.

The non-aqueous liquid in one preferred set of embodiments is selected from water-immiscible liquids, particularly organic water-immiscible, surfactants (which may be water miscible or water immiscible and may be dissolved in the water immiscible liquid) and mixtures of two or more thereof. The more preferred non-aqueous liquid comprises a water immiscible liquid and surfactant. The non-aqueous liquid, which is mixed with the granular carrier, may comprise a water component, such as up to 10% water by weight of the non-aqueous liquid, but does not constitute part of the non-aqueous liquid.

Throughout the description and the claims of this specification the word "comprise" and variations of the word, such as "comprising" and "comprises" is not intended to exclude other additives, components, integers or steps.

The term average individual granule density is used herein to refer to the density of the composition in the granules and is distinguished from the packing density of the granules.

Where referred to herein the density of materials is determined at 20° C.

The term packing density of the granules refers to the density of a composition of granules and includes the inter-granule spaces in the composition. The packing density is used to measure the space efficiency with which granules may be transported and delivered, for example, from an aircraft.

The term water-immiscible liquid where used herein refers to a liquid which fails to dissolve in water when mixed with water in an amount of 10% water-immiscible liquid w/w of the mixture at 20° C. Failure to dissolve means the liquid forms a separate phase which may be a discrete layer or a fine dispersion of droplets of the liquid in the water (i.e. a self-dispersion). The water immiscible liquid preferably fails to dissolve in water at 3% w/w and preferably at 0.3% water-immiscible liquid w/w of the mixture.

The term sorbed includes adsorbed and absorbed.

DETAILED DESCRIPTION

In one set of embodiments the insecticidal granular composition comprises:

from 60% to 95% w/w (preferably 70% to 90% w/w) of the granular carrier;

from 1% to 30% w/w (preferably 3% to 20% w/w) non-aqueous liquid; and from $2\times10^6$ to $100\times10^6$ International Toxicology Units (ITU) per 100 g of granules preferably $3\times10^6$ to $60\times10^6$ and more preferably from $7.5\times10^6$ to $20\times10^6$ ITU per 100 g of granules.

In one set of embodiments the insecticidal granular composition comprises:

from 60% to 95% w/w (preferably 70% to 90% w/w) of the granular carrier;

from 3% to 20% w/w non-aqueous liquid; and from 0.5% to 7% w/w of larvicidal active having a specific activity of 3000 to 8000 International Toxicology Units (ITU) per milligram, preferably from 1.5% to 6% w/w of larvicidal active having from 4000 to 6000 ITU per milligram.

The insecticidal granular composition may and preferably will comprise a binder. A binder component is included in the granules as necessary to reduce powder formation during storage and handling and/or to reduce loss of the active larvicide which is concentrated toward the outer surface of the granules. A binder component illustratively includes carbohydrate, protein, lipid, synthetic polymer, glycolipid, glycoprotein, lipoprotein, lignin, a lignin derivative, a carbohydrate-based composition, and a combination thereof. In a preferred embodiment the binder component is a lignin derivative and is optionally calcium lignosulfonate. The binder component may comprise one or more selected from the group consisting of: a monosaccharide, a disaccharide, an oligosaccharide and polysaccharide. Specific carbohydrate binders illustratively include glucose, mannose, fructose, galactose, sucrose, lactose, maltose, xylose, arabinose, trehalose and mixtures thereof such as corn syrup; celluloses such as carboxymethylcellulose, ethylcellulose, hydroxyethylcellulose, hydroxy-methylethylcellulose, hydroxyethylpropylcellulose, methylhydroxyethyl-cellulose, methylcellulose; starches such as amylose, seagel, starch acetates, starch hydroxyethyl ethers, ionic starches, long-chain alkyl starches, dextrins, amine starches, phosphates starches, and di-aldehyde starches; plant starches such as corn starch and potato starch; other carbohydrates such as pectin, amylopectin, xylan, glycogen, agar, alginic acid, phycocolloids, chitin, gum arabic, guar gum, gum karaya, gum tragacanth and locust bean gum; vegetable oils such as corn, soybean, peanut, canola, olive and cotton seed; complex organic substances such as lignin and nitrolignin; derivatives of lignin such as ligno sulfonate salts illustratively including calcium ligno sulfonate and sodium ligno sulfonate and complex carbohydrate-based compositions containing organic and inorganic ingredients such as molasses. Suitable protein binders illustratively include soy extract, zein, protamine, collagen, and casein. Binders also include synthetic organic polymers capable of promoting or producing cohesion of particle components and such binders illustratively include ethylene oxide polymers, polyacrylamides, polyacrylates, polyvinyl pyrrolidone, polyethylene glycol, polyvinyl alcohol, polyvinylmethyl ether, polyvinyl acrylates, polylactic acid, and latex. In a preferred embodiment, the binder is calcium lignosulfonate, molasses, a liquid corn starch, a liquid corn syrup or a combination thereof.

Water-dispersible polymers may optionally be used as a binder and form a coating on the granules. The water-dispersible polymers preferably have a molecular weight of more than 1,500 and are water soluble or at least water suspendable. The water-dispersible polymers illustratively include polyvinyl alcohols (PVA), polyethylene glycols (PEG), polyethylene oxides (PEO), polyvinyl pyrrolidones (PVP), cellulose ethers, alginates, gelatin, modified starches and substituted derivatives, hydrolysates and copolymers thereof. Most preferred polymers are PVA, cellulose ethers, such as methyl cellulose and hydroxylpropyl cellulose, gelatin and modified starches, such as hydroxypropyl starch produced from cornstarch.

Examples of more preferred binders include a polysaccharides or modified polysaccharide (such as hydroxypropylmethylcellulose). The binder may be present in an amount of from 0% to 3% by weight of the composition and in a preferred set of embodiments is present in an amount of from 0.2% to 2% by weight of the insecticidal granular composition. The binder may be added as an aqueous composition but the amount of binder is determined on the basis of the binder content of the aqueous composition and not of the total aqueous composition. In one embodiment the binder is delivered as an aqueous spray.

In the process aspect the larvicide may be mixed with the liquid components including the binder or alternatively the larvicidal active may be may be mixed with the liquid components, not including the binder. In the latter case the liquid components, including the suspended larvicide, are sorbed onto/into the granules and the binder subsequently added. We have found the presence of a binder may significantly reduce the loss of larvicide during storage and handling of the granules.

The sorption of the suspended larvicide into the granule has been found to provide an outer or shell region of granule which has a relatively high proportion of the larvicide and an inner or core region of the granules with a relatively low proportion of the larvicide.

The relatively high concentration of the larvicide in the outer part of the individual granules may be confirmed by removing some of the outer portion of the granules by erosion or attrition and comparing the concentration of larvicide in the removed outer portion with the concentration of larvicide in crushed whole granules from the same granular composition (i.e. the average concentration over the entire granule). A higher concentration in the outer material, particularly by an amount of at least 20%, shows a core shell morphology. Typically, assays for the larvicidal active agent, such as protein assays in the case of biological larvicides such as Bt or Bs, taken from granule outer portion or shell as, for example as shavings or attrition products, show significantly more larvicidal protein than protein assays from whole granules. Granule shavings/attrition products are fine materials formed when the granules are loaded into a container with attrition media and the container is rolled for a defined time period (see Example 11). In one set of embodiments the protein content of granule outer shell is at least 1.25 times greater than the protein content of whole granules. More preferably the protein content of granule shavings is at least 1.5 times greater than the protein content of whole granules.

The non-aqueous liquid preferably comprises a water immiscible liquid, a surface active agent or a water-immiscible liquid and surface active agent which is preferably soluble in the water immiscible liquid. The surface active agent component may comprise one or more surfactants and in a preferred set of embodiments comprises a nonionic surface active agent, an alkylarylsulfonate such as dodecylbenzenesulfonate or mixture of two or more thereof. Examples of non-ionic surfactants include ethoxylated sorbitan esters such as EMSORB, TWEEN, and T-MAZE; ethoxylated sorbitan fatty acid esters such as ECOTERIC T80 (polyoxyethylene(20)sorbitan monooleate), SPAN and ALKAMUL; sucrose and glucose esters and derivatives thereof such as MAZON, RHEOZAN and GLUCOPON; ethoxylated alcohols such as TRYCOL, BRIJ, ARMIX and PLURAFAC; ethoxylated alkylphenols such as IGEPAL, MACOL and TERGITOL; ethoxylated fatty amines such as TRYMEEN and ETHOMEEN; ethoxylated fatty acids such as EMEREST, ALKAMUL and TRYDET; ethoxylated fatty esters and oils such as ALKAMUL and ATLAS G; fatty acids such as ATLAS G-1556; glycerol esters such as MAZOL GMO; glycol esters such as GLYCOL SEG; lanolin-based derivatives such as AMERCHOL CAB; methyl esters such as OLEOCAL ME; monoglycerides and derivatives such as ETHOSPERSE G-26; propoxylated and ethoxylated fatty acids such as ANTAROX AA-60; block copolymers of ethylene oxide and propylene oxide such as PLURONIC or SURFONIC; silicone-based surfactants such as SILWET, BREAKTHRU and mixtures of organosilicon surfactant with non-ionic or ionic surfactants; polysaccharides, copolymers of acrylamide and acrylic acid; and acetylenic diol derivatives such as SURFYNOL 104 or tristyrylphenols such as SOPROPHOR among others.

The total surface active agent component is preferably present in an amount of from 0.3% to 5% w/w of the insecticidal granular composition.

The larvicidal active present in the insecticidal granular composition is preferably *Bacillus thuringiensis, Bacillus sphaericus* or a mixture thereof, more preferably *Bacillus thuringiensis* var. *Israelensis*. Most preferably the larvicidal active is *Bacillus thuringiensis* var. *Israelensis* of serotype H-14. These actives may be natural occurring proteins or spores or genetically modified proteins or spores. The larvicidal active may be used in any suitable form. In one set of embodiments the larvicidal active is in the form of a technical powder or wettable powder comprising additives to render the powder wettable on addition of water.

We have found that the efficacy of the composition in delivering the active larvicide to the water surface is enhanced by providing the granule with a core-shell character such that the outer region of the granule is richer in larvicidal active relative to the inner region of the granule.

The non-aqueous liquid preferably comprises a water-immiscible liquid, a surfactant or most preferably a mixture of the two. The non-aqueous liquid is preferably a water-immiscible organic liquid. The non-aqueous liquid has a density less than 1 and preferably has a density in the range of from 0.75 to 0.99 g/ml, more preferably 0.80 to 0.95 g/ml. Preferred examples of the water-immiscible liquid are selected from the group consisting of paraffin oil, kerosene and vegetable oils. Examples of preferred surfactants include fatty alkyl ethoxylates and may be larvicidal such as an ethoxylated fatty alcohol (e.g. ethoxylated $C_{13}$ alcohol, such as SYMPERONIC C13/5). In one embodiment the water-immiscible liquid comprises one or more selected from the group consisting of vegetable oils and/or esters thereof, paraffinic oil and a lighter petroleum oil fraction. In one set of embodiments the non-aqueous liquid comprises a liquid which has larvicidal activity in its own right.

In one set of embodiments of the invention the ratio of bacterially derived lavicide to non-aqueous liquid (preferably water-immiscible liquid, surfactant or mixture thereof) is in the range of from 8% to 50% by weight.

The granular carrier component of the insecticidal granular composition typically has a sorption capacity for the non-aqueous liquid of at least 3% by weight and preferably at least 5% by weight. The sorption capacity may be up to 30% by weight (preferably up to 20% by weight). Examples of suitable granular carriers include clay, preferably attapulgite, bentonite or a mixture thereof and most preferably bentonite. The more preferred granular carrier comprises bentonite in the form of sodium bentonite, potassium bentonite, calcium bentonite or a mixed cation form of bentonite comprising at least two of sodium potassium and calcium cations. It is preferred that the insecticidal granular composition comprises a non-agglomerated carrier. While agglomeration has been used to incorporate active agents into granules such incorporation results in even distribution of the active within the granule and leads to granules of relatively poor strength compared with non-agglomerated granules prepared by milling carrier material to the desired size range which may be isolated by screening. It is preferred that the solid carrier used in preparing the granule composition is not an agglomerate, that is, the granule composition is of primary particles onto which the liquor comprising active agent is absorbed without agglomeration of the particles. In other words the particles are un-agglomerated primary particles as distinct from secondary particles formed by agglomeration of primary powder particles much finer than the secondary particles. Granules formed without agglomeration are generally less susceptible to formation of fines and are more effective in delivering the larvicide by broadcasting of the solid granules. The carrier granules may be prepared by crushing larger sized material and sieving to provide the required carrier particle size without the need to agglomerate fines.

Good control of insects may be compromised by too sparse a distribution of granules and increasing the loading of active has the potential to either waste the active or provide hot spots of concentration which are too widely spaced to control the target insect population. It is preferred that at least 80% w/w of the composition comprises granules having an aspect ratio (largest dimension/smallest dimension) in the range of from 1 to 1.5. Granules of this aspect ratio have ballistic properties that allow accurate positioning by aerial distribution and allow good insect control with an economic payload of granules. The packing density of insecticidal granular composition is preferably at least 0.7 g per cubic centimeter, more preferably at least 0.8 g per cubic centimeter and most preferably at least 0.9 g per cubic centimeter.

The granular carrier preferably disintegrates in water within a period of no more than 60 minutes.

The insecticidal granular composition may be prepared from a suspension of the bacterially derived larvicidal active in the non-aqueous liquid by absorption into the granular carrier.

In one aspect there is provided a process for preparation of an insecticidal granular composition for broadcasting on a body of water, comprising:

providing a granular carrier of size in the range of form 1 to 4 mm; and mixing the carrier with a suspension of larvicidal active in a non-aqueous liquid to absorb the suspension into the granules;

wherein the non-aqueous liquid has a density less than 1 and the insecticidal granular composition has an average individual granule density greater than 1 and is adapted to sink in the body of water.

The granular carrier is preferably of particle size of 1 to 4 mm. It is also preferred that the granular carrier is not formed by agglomeration from powders or particles of smaller size. The granular carrier component of the insecticidal granular composition typically has a sorption capacity for the non-aqueous liquid of at least 3% by weight and preferably at least 5% by weight. The sorption capacity may be up to 30% by weight (preferably up to 20% by weight). Examples of suitable granular carriers include clay, preferably attapulgite, bentonite or a mixture thereof and most preferably bentonite.

The suspension used in the preparation of the insecticidal granular composition preferably comprises a weight ratio of bacterially derived larvicidal active to non-aqueous liquid in the range of from 5% to 60% (preferably 8% to 50%) by weight active based on the weight of non-aqueous liquid. The non-aqueous liquid in which the larvicidal active is dispersed may and preferably will comprise a surfactant. In determining the weight ratio of larvicide to liquid carrier the surfactant, when present is part of the non-aqueous liquid.

The granular carrier and suspension may be mixed using a range of mixing apparatus but we have found the best results are obtained when the carrier and suspension are mixed in a rotating drum mixer. Examples of suitable rotating drum mixers are those used in preparation of mortar and concrete and may be fixed or mobile mixers of a range of capacities such as from 1 to 5 cubic meters.

In a further aspect there is provided a method for the control of insects on a body of water, comprising applying to the body of water an insecticidal granular composition as herein before described. In one set of embodiments the insecticidal granular composition is applied to the body of water at a rate of from $100 \times 10^6$ to $5000 \times 10^6$ ITU/ha, preferably $150 \times 10^6$ to $2000 \times 10^6$ ITU/ha.

The granules of the invention may comprise more than one pesticide with activity against one or more of the life stages of mosquitoes. These granules will be referred to as co-formulated granules.

Co-formulated granules may comprise more than one bio-insecticide, for example *Bacillus thuringiensis* and *Bacillus sphaericus* moieties (toxins or cells or toxins and cells).

Co-formulated granules may comprise a bio-insecticide and one or more further insecticides. In one preference these further insecticides may be chosen from the set consisting of methoprene, s-hydroprene, s-kinoprene, s-methoprene, pyriproxyfen, temephos, larvicidal oils, surface active agents with a capacity to form monomolecular layers. Examples of larvicidal oils include methoprene.

Examples of surface active agents with a capacity to form monomolecular layers include ethoxylated fatty alcohols (e.g. $C_{13}$ alcohol, such as SYNPERONIC C13/5).

In one preferment, the further insecticide may comprise at least one of methoprene and pyriproxyfen. The preferred amounts of the further insecticide may be amounts which would provide insecticidal activity independently of the biological larvicide or may be used in a lesser amount which provides activity in combination with the biological larvicide.

The insecticidal granular composition may be broadcast by dispensing from adjacent the ground but the insecticidal granular composition is particularly suited to being broadcast from an aircraft such as a fixed wing aircraft or preferably a helicopter. In a preferred set of embodiments the granular composition is applied from a helicopter having an application speed of at least 70 km/hr and a granule carrying capacity of greater than 150 kg. In one preferred set of embodiments the granules are applied using a helicopter having an application speed of greater than 80 Km/hr and a granule capacity of greater than 200 Kg.

In one set of embodiments the granules are applied using a fixed wing aircraft having an application speed of greater than 150 Km/hr and a granule capacity of greater than 1500 liters.

In a further set of embodiments the granules are applied from a fixed-wing aircraft wherein the area treated per hopper load is greater than 150 hectares (preferably greater than 200 hectares and more preferably greater than 210 hectares).

In a set of embodiments the granules are applied from a helicopter wherein the area treated per hopper load is greater than 25 hectares (preferably greater than 30 and more preferably greater than 35 hectares).

The invention will now be described with reference to the following examples. It is to be understood that the examples are provided by way of illustration of the invention and that they are in no way limiting to the scope of the invention.

EXAMPLES

In the Examples, specification and claims the following standard abbreviations are used:
ITU—International Toxic Units
ha—hectares
g—grams; ml—milliliters; cm—centimeters; kg—kilograms and mg—milligrams In the examples the reference to parts means parts by weight.

Example 1

Formulation A

The formulation components were
Btl wettable powder (5000 ITU/mg) CAS#2712-78-9 quantity 20 parts (sourced from Pacific Agriscience, Tanjong Pagar Rd, Singapore)
Caltex RD2910 oil [light mineral oil, density approx. 0.83 g/ml; viscosity at 40° C., cSt (ASTMD 445) is 12.3; pour point (ASTM D97) is −21° C. max; Total acid no. is <1 mg KOH/g typically; Sulfur (ASTMD2622) is typically <1 ppm, quantity 176 parts
Maltodextrin aqueous solution (25 w/w %) CAS#9050-36-6 quantity 20 parts (acts to adhere Btl to base granule)
Attapulgite CAS#12174-11-7 quantity 784 parts (preformed base granule, 1-3 mm).

In measuring the weight ratio of larvicide to non-aqueous liquid the surfactant, when present, is considered part of the non-aqueous liquid.

In formulation preparation, step 1 is to prepare the maltodextrin solution by dissolving 250 g powder in 750 g of warm water (40° C.). The solution is allowed to cool to ambient, and weighed. Water lost to evaporation is replaced. Step 2 is to add 17.6 kg of attapulgite granules to a cement mixer. Step 3 is to add 4.4 kg of oil and 0.5 kg Btl technical powder to a vessel, with gentle mixing to form a dispersion free of lumps. The resultant liquor is transferred to a multi-orifice watering can. Step 4 is to set the cement mixer in motion and to slowly add the Btl oil dispersion to the moving mass of granules through the spout of the multi-orifice watering can. Thereafter 500 g of maltodextrin solution is added, with further mixing until all lumps have disappeared. Step 5 is to carry out QA tests and subject to QA clearance to pack the material off. The quality protocol includes (i) appearance—the target specification is ("brown granules"), (ii) pH (1% w/w solution)—the target specification is 5-7, (iii) packing density—the target specification is 0.967+/−0.003 g/ml, (iv) flowability—the target specification is "free flowing", (v) active agent concentration Btl—the target specification is 17-23 g/kg.

100 g of attapulgite granules had an oil sorption capacity of 19.6 g oil.

Example 2

Formulation B

The formulation components were
Btl wettable powder (5000 ITU/mg) CAS#2712-78-9 quantity 20 parts (sourced from Pacific Agriscience, Tanjong Pagar Rd, Singapore). Btl grown in culture centrifuged to sludge and spray dried.
Methoprene oil CAS#40596-69-8 quantity 176 parts. Methoprene is a larvicidal oil which floats on water.
Maltodextrin aqueous solution (25% w/w) CAS#9050-36-6 quantity 20 parts (acts to adhere Btl to base granule)
Attapulgite CAS#12174-11-7 quantity 784 parts (preformed base granule, 1-3 mm)

In formulation preparation, step 1 is to prepare the maltodextrin solution by dissolving 250 g powder in 750 g of warm water (40° C.). The solution is allowed to cool to ambient, and weighed. Water lost to evaporation is replaced. Step 2 is to add 17.6 kg of attapulgite granules to a cement mixer. Step 3 is to add 4.4 kg of methoprene oil and 0.5 kg Btl technical powder to a vessel, with gentle mixing to form a dispersion free of lumps. The resultant liquor is transferred to a multi-orifice watering can. Step 4 is to set the cement mixer in motion and to slowly add the Btl oil dispersion to the moving mass of granules through the spout of the multi-orifice watering can. Thereafter 500 g of maltodextrin solution is added, with further mixing until all lumps have disappeared. Step 5 is to carry out QA tests and subject to QA clearance to pack the material off. The quality protocol includes (i) appearance—the target specification is "brown granules"), (ii) pH (1% w/w solution)—the target specification is 5-7, (iii) packing density—the target specification is 0.967+/−0.003 g/ml, (iv) flowability—the target specification is "free flowing", (v) active agent concentration Btl —the target specification is 17-23 g/kg.

Example 3

Formulation C

The formulation components were
Btl wettable powder (5000 ITU/mg) CAS#2712-78-9, quantity 20 parts (sourced from Pacific Agriscience, Tanjong Pagar Rd, Singapore). Btl grown in culture, centrifuged to sludge and spray dried.
Synperonic 13/5 (oil) 176 parts. Synperonic 13/5 is an ethoxylated primary branched C13 alcohol made by Croda, with a HLB of 11.2. This oil forms a thin layer over an air-water interface, and has larvicidal activity in its own right.
Maltodextrin aqueous solution (25 w/w %) CAS#9050-36-6 quantity 20 parts (acts to adhere Btl to base granule)
Attapulgite CAS#12174-11-7 quantity 784 parts (preformed base granule, 1-3 mm)

In formulation preparation, step 1 is to prepare the maltodextrin solution by dissolving 250 g powder in 750 g of warm water (40° C.). The solution is allowed to cool to ambient, and weighed. Water lost to evaporation is replaced. Step 2 is to add 17.6 kg of attapulgite granules to a cement mixer. Step 3 is to add 4.4 kg of Synperonic 13/5 oil and 0.5 kg Btl technical powder to a vessel, with gentle mixing to form a dispersion free of lumps. The resultant liquor is transferred to a multi-orifice watering can. Step 4 is to set the cement mixer in motion and to slowly add the Btl oil dispersion to the moving mass of granules through the spout of the multi-orifice watering can. Thereafter 500 g of maltodextrin solution is added, with further mixing until all lumps have disappeared. Step 5 is to carry out QA tests and subject to QA clearance to pack the material off. The quality protocol includes (i) appearance—the target specification is "brown granules"), (ii) pH (1% w/w solution)—the target specification is 5-7, (iii) packing density—the target specification is 0.967+/−0.003 g/ml, (iv) flowability—the target specification is "free flowing", (v) active agent concentration Btl—the target specification is 17-23 g/kg.

Example 4

Formulation D

The formulation components were
Btl wettable powder (5000 ITU/mg) CAS#2712-78-9 quantity 20 parts (sourced from Pacific Agriscience, Tanjong Pagar Rd, Singapore). Btl grown in culture, centrifuged to sludge and spray dried.
Low-odour kerosene (light oil) provided by Oil Chem Australia CAS#8008-20-6 176 parts.
Maltodextrin aqueous solution (25% w/w) CAS#9050-36-6 quantity 20 parts (acts to adhere Btl to base granule)
Attapulgite CAS#12174-11-7 quantity 784 parts (preformed base granule, 1-3 mm)

In formulation preparation, step 1 is to prepare the maltodextrin solution by dissolving 250 g powder in 750 g of warm water (40° C.). The solution is allowed to cool to ambient, and weighed. Water lost to evaporation is replaced. Step 2 is to add 17.6 kg of attapulgite granules to a cement mixer. Step 3 is to add 4.4 kg of low-odour kerosene and 0.5 kg Btl technical powder to a vessel, with gentle mixing to form a dispersion free of lumps. The resultant liquor is transferred to a multi-orifice watering can. Step 4 is to set the cement mixer in motion and to slowly add the Btl oil dispersion to the moving mass of granules through the spout of the multi-orifice watering can. Thereafter 500 g of maltodextrin solution is added, with further mixing until all lumps have disappeared. Step 5 is to carry out QA tests and subject to QA clearance to pack the material off. The quality protocol includes (i) appearance—the target specification is "brown granules"), (ii) pH (1% w/w solution)—the target specification is 5-7, (iii) packing density—the target specification is 0.967+/−0.003 g/ml, (iv) flowability—the target specification is "free flowing", (v) active agent concentration Btl—the target specification is 17-23 g/kg.

Example 5

Formulation E1

The formulation components were
Btl wettable powder (5000 ITU/mg) CAS#2712-78-9 quantity 22.8 parts (sourced from Pacific Agriscience, Tanjong Pagar Rd, Singapore). Btl grown in culture, centrifuged to sludge and spray dried.
Synperonic 13/5 (oil) provided by Croda 65 parts.

Ecoteric T80 (polyoxyethylene(20)sorbitan monooleate (CAS 9005-65-6) surfactant 5 parts Maltodextrin aqueous solution (25% w/w) CAS#9050-36-6 quantity 20 parts (acts to adhere Btl to base granule)

Bentonite (calcium/sodium form, Trufeed made by Unimin, sieved to retain granules in the range 0.5-1 mm, quantity 887.2 parts (pre-formed base granule). On submersion in water, these granules lost structure and disperse within 1 hour.

In formulation preparation, step 1 is to prepare the maltodextrin solution by dissolving 250 g powder in 750 g of warm water (40° C.). The solution is allowed to cool to ambient, and weighed. Water lost to evaporation is replaced. Step 2 is to add 17.6 kg of bentonite granules to a cement mixer. Step 3 is to add Synperonic, Ecoteric T 80 and Btl technical powder to a vessel, with gentle mixing to form a dispersion free of lumps. The resultant liquor is transferred to a multi-orifice watering can. Step 4 is to set the cement mixer in motion and to slowly add the Btl/oil/Ecoteric T80 dispersion to the moving mass of granules through the spout of the multi-orifice watering can. Thereafter 500 g of maltodextrin solution is added, with further mixing until all lumps have disappeared. Step 5 is to carry out QA tests and subject to QA clearance to pack the material off. The quality protocol includes (i) appearance—the target specification is "brown granules"), (ii) pH (1% w/w solution)—the target specification is 5-7, (iii) packing density—the target specification is 0.967+/−0.003 g/ml, (iv) flowability—the target specification is "free flowing", (v) active agent concentration Btl—the target specification is 17-23 g/kg.

Example 6

Formulation E2

The formulation components were

Btl technical (5000 ITU/mg) CAS#2712-78-9 quantity 22.8 parts (sourced from Pacific Agriscience, Tanjong Pagar Rd, Singapore). Btl grown in culture, centrifuged to sludge and spray dried.

Light mineral oil (paraffinic; density 0.83 g/ml)) 35 parts.

Ecoteric T80 surfactant 5 parts

Maltodextrin aqueous solution (25% w/w) CAS#9050-36-6 quantity 20 parts (acts to adhere Btl to base granule)

Black attapulgite sourced from India, 920.0 parts.

In formulation preparation, step 1 is to prepare the maltodextrin solution by dissolving 250 g powder in 750 g of warm water (40° C.). The solution is allowed to cool to ambient, and weighed. Water lost to evaporation is replaced. Step 2 is to add 17.6 kg of bentonite granules to a cement mixer. Step 3 is to add light mineral oil, Ecoteric T80 and Btl technical powder to a vessel, with gentle mixing to form a dispersion free of lumps. The resultant liquor is transferred to a multi-orifice watering can. Step 4 is to set the cement mixer in motion and to slowly add the Btl/oil/Ecoteric T80 dispersion to the moving mass of granules through the spout of the multi-orifice watering can. Thereafter 500 g of maltodextrin solution is added, with further mixing until all lumps have disappeared.

Example 7

Formulation E3

The formulation components were

Btl wettable powder (5000 ITU/mg) CAS#2712-78-9 quantity 20 parts (sourced from Pacific Agriscience, Tanjong Pagar Rd, Singapore). Btl grown in culture, centrifuged to sludge and spray dried.

Heavy mineral oil (paraffinic, density 0.905 g/ml) 35 parts.

Ecoteric T80 surfactant 5 parts

Maltodextrin aqueous solution (25 w/w %) CAS#9050-36-6 quantity 20 parts (acts to adhere Btl to base granule)

Bentonite (calcium/sodium form, Trufeed made by Unimin, sieved to retain granules in the range 2-3 mm, quantity 920 parts (pre-formed base granule). On submersion in water, these granules lost structure and disperse within 1 hour.

In formulation preparation, step 1 is to prepare the maltodextrin solution by dissolving 250 g powder in 750 g of warm water (40° C.). The solution is allowed to cool to ambient, and weighed. Water lost to evaporation is replaced. Step 2 is to add 17.6 kg of bentonite granules to a cement mixer. Step 3 is to add heavy mineral oil, Ecoteric T80 and Btl technical powder to a vessel, with gentle mixing to form a dispersion free of lumps. The resultant liquor is transferred to a multi-orifice watering can. Step 4 is to set the cement mixer in motion and to slowly add the Btl/oil/Ecoteric T80 dispersion to the moving mass of granules through the spout of the multi-orifice watering can. Thereafter 500 g of maltodextrin solution is added, with further mixing until all lumps have disappeared. Step 5 is to carry out QA tests and subject to QA clearance to pack the material off. The quality protocol includes (i) appearance—the target specification is "brown granules"), (ii) pH (1% w/w solution)—the target specification is 5-7, (iii) packing density—the target specification is 0.967+/−0.003 g/ml, (iv) flowability—the target specification is "free flowing", (v) active agent concentration Btl—the target specification is 17-23 g/kg.

Example 8

Formulation E4

The formulation components were

Btl wettable powder (5000 IU/mg) CAS#2712-78-9 quantity 22.8 parts (sourced from Pacific Agriscience, Tanjong Pagar Rd, Singapore). Btl grown in culture, centrifuged to sludge and spray dried.

Methoprene oil 68 parts.

Ecoteric T80 surfactant 5 parts

Maltodextrin aqueous solution (25 w/w %) CAS#9050-36-6 quantity 20 parts (acts to adhere Btl to base granule)

Bentonite (calcium/sodium form, Trufeed made by Unimin, sieved to retain granules in the range 1-2 mm, quantity 884.4 parts (pre-formed base granule). On submersion in water, these granules lost structure and disperse within 1 hour.

In formulation preparation, step 1 is to prepare the maltodextrin solution by dissolving 250 g powder in 750 g of warm water (40° C.). The solution is allowed to cool to ambient, and weighed. Water lost to evaporation is replaced. Step 2 is to add 17.6 kg of bentonite granules to a cement mixer. Step 3 is to add heavy mineral oil, Ecoteric T80 and Btl technical powder to a vessel, with gentle mixing to form a dispersion free of lumps. The resultant liquor is transferred to a multi-orifice watering can. Step 4 is to set the cement mixer in motion and to slowly add the Btl/oil/Ecoteric T80 dispersion to the moving mass of granules through the spout of the multi-orifice watering can. Thereafter 500 g of maltodextrin solution is added, with further mixing until all lumps have disappeared. Step 5 is to carry out QA tests and subject to QA clearance to pack the material off. The quality protocol includes (i) appearance—the target specification is "brown granules"), (ii) pH (1% w/w solution)—the target specification is 5-7, (iii) packing density—the target specification is 0.967+/−0.003 g/ml, (iv) flowability—the target specification is "free flowing", (v) active agent concentration Btl—the target specification is 17-23 g/kg.

Note: adhesive solution can also be Rutocel (hydroxypropylmethylcellulose)

Example 9

Bioefficacy Data

Tables 1 to 3 in this example provide bioefficacy date for compositions described in Examples 1 to 8. In particular:

Table 1 provides efficacy data for formulations A-D (from Examples 1 to 4) on Brown House mosquito.

Table 2 provides efficacy data for formulations A-D (from Examples 1 to 4) on Dengue mosquito.

Table 3 provides efficacy data for formulations E1-E4 (from Examples 5 to 8) on Dengue mosquito.

With reference to the tables it can be seen that:

Substantial efficacy was observed for all compositions at 48 hours.

At 12 hours following application formulations A-D were in general less efficacious than E1 to E4 in terms of percent mortality. Granules of the invention which disintegrate in water and contain an oil phase containing a surface active agent had the most rapid activity.

The activity of Btl wettable powder and "Vectobac" granules was also examined and reported in the tables. "Vectobac" granules are a commercially available granules based on Btl active larvicide absorbed on a corn grit carrier having a density less than 1 so that the granules float on water. An untreated control was also examined and gave rise to zero mortality under the conditions of the trials.

TABLE 1

| Treatment | Rate mL/L | Rep. | 4 Hours | | | | 6 Hours | | | | 8 Hours | | | |
|---|---|---|---|---|---|---|---|---|---|---|---|---|---|---|
| | | | A | K | D | %M | A | K | D | %M | A | K | D | %M |
| 1. Formulation A | 9.8 kg/ha | 1 | 20 | 0 | 0 | 0 | 19 | 1 | 0 | 5 | 17 | 0 | 3 | 15 |
| | | 2 | 20 | 0 | 0 | 0 | 20 | 0 | 0 | 0 | 20 | 0 | 0 | 0 |
| | | 3 | 20 | 0 | 0 | 0 | 20 | 0 | 0 | 0 | 18 | 0 | 2 | 10 |
| | | 4 | 20 | 0 | 0 | 0 | 20 | 0 | 0 | 0 | 17 | 0 | 3 | 15 |
| | | Mean | | | | 0.0 | | | | 1.3 | | | | 10.0 |
| 2. Formulation B | 9.8 kg/ha | 1 | 20 | 0 | 0 | 0 | 19 | 1 | 0 | 5 | 19 | 0 | 1 | 5 |
| | | 2 | 20 | 0 | 0 | 0 | 18 | 2 | 0 | 10 | 15 | 0 | 5 | 25 |
| | | 3 | 20 | 0 | 0 | 0 | 20 | 0 | 0 | 0 | 19 | 0 | 1 | 5 |
| | | 4 | 20 | 0 | 0 | 0 | 17 | 3 | 0 | 15 | 14 | 0 | 6 | 30 |
| | | Mean | | | | 0.0 | | | | 7.5 | | | | 16.3 |
| 3. Formulation C | 9.8 kg/ha | 1 | 20 | 0 | 0 | 0 | 20 | 0 | 0 | 0 | 20 | 0 | 0 | 0 |
| | | 2 | 20 | 0 | 0 | 0 | 20 | 0 | 0 | 0 | 20 | 0 | 0 | 0 |
| | | 3 | 20 | 0 | 0 | 0 | 20 | 0 | 0 | 0 | 20 | 0 | 0 | 0 |
| | | 4 | 20 | 0 | 0 | 0 | 20 | 0 | 0 | 0 | 20 | 0 | 0 | 0 |
| | | Mean | | | | 0.0 | | | | 0.0 | | | | 0.0 |
| 4. Formulation D | 9.8 kg/ha | 1 | 20 | 0 | 0 | 0 | 20 | 0 | 0 | 0 | 18 | 0 | 2 | 10 |
| | | 2 | 20 | 0 | 0 | 0 | 19 | 1 | 0 | 5 | 19 | 0 | 1 | 5 |
| | | 3 | 20 | 0 | 0 | 0 | 20 | 0 | 0 | 0 | 19 | 0 | 1 | 5 |
| | | 4 | 20 | 0 | 0 | 0 | 20 | 0 | 0 | 0 | 18 | 0 | 2 | 10 |
| | | Mean | | | | 0.0 | | | | 1.3 | | | | 7.5 |
| 5. WP Bti | 9.8 kg/ha | 1 | 0 | 20 | 0 | 100 | 0 | 0 | 20 | 100 | 0 | 0 | 20 | 100 |
| | | 2 | 0 | 20 | 0 | 100 | 0 | 0 | 20 | 100 | 0 | 0 | 20 | 100 |
| | | 3 | 0 | 20 | 0 | 100 | 0 | 0 | 20 | 100 | 0 | 0 | 20 | 100 |
| | | 4 | 0 | 20 | 0 | 100 | 0 | 0 | 20 | 100 | 0 | 0 | 20 | 100 |
| | | Mean | | | | 100.0 | | | | 100.0 | | | | 100.0 |
| 6. Vectobac | 7.0 kg/ha | 1 | 14 | 6 | 0 | 30 | 7 | 13 | 0 | 65 | 2 | 1 | 17 | 90 |
| | | 2 | 15 | 5 | 0 | 25 | 10 | 11 | 0 | 52 | 3 | 0 | 17 | 85 |
| | | 3 | 16 | 4 | 0 | 20 | 8 | 12 | 0 | 60 | 5 | 0 | 15 | 75 |
| | | 4 | 14 | 6 | 0 | 30 | 5 | 15 | 0 | 75 | 3 | 0 | 17 | 85 |
| | | Mean | | | | 26.3 | | | | 63.1 | | | | 83.8 |

| Treatment | Rate mL/L | Rep. | 12 Hours | | | | 24 Hrs | | | | 48 Hrs | | | |
|---|---|---|---|---|---|---|---|---|---|---|---|---|---|---|
| | | | A | K | D | %M | A | K | D | %M | A | K | D | %M |
| 1. Formulation A | 9.8 kg/ha | 1 | 15 | 0 | 5 | 25 | 9 | 0 | 11 | 55 | 4 | 0 | 16 | 80 |
| | | 2 | 18 | 0 | 2 | 10 | 10 | 0 | 10 | 50 | 6 | 0 | 14 | 70 |
| | | 3 | 16 | 0 | 4 | 20 | 9 | 0 | 11 | 55 | 3 | 0 | 17 | 85 |
| | | 4 | 15 | 0 | 5 | 25 | 12 | 0 | 8 | 40 | 4 | 0 | 16 | 80 |
| | | Mean | | | | 20.0 | | | | 50.0 | | | | 78.8 |
| 2. Formulation B | 9.8 kg/ha | 1 | 12 | 0 | 8 | 40 | 2 | 0 | 18 | 90 | 1 | 0 | 19 | 95 |
| | | 2 | 13 | 0 | 7 | 35 | 1 | 0 | 19 | 95 | 0 | 0 | 20 | 100 |
| | | 3 | 17 | 0 | 3 | 15 | 2 | 0 | 18 | 90 | 0 | 0 | 20 | 100 |
| | | 4 | 12 | 0 | 8 | 40 | 2 | 0 | 18 | 90 | 0 | 0 | 20 | 100 |
| | | Mean | | | | 32.5 | | | | 91.3 | | | | 98.8 |
| 3. Formulation C | 9.8 kg/ha | 1 | 18 | 0 | 2 | 10 | 13 | 0 | 7 | 35 | 3 | 0 | 17 | 85 |
| | | 2 | 19 | 0 | 1 | 5 | 14 | 0 | 6 | 30 | 2 | 0 | 18 | 90 |

TABLE 1-continued

| | | | | | | | | | | | | | | | | |
|---|---|---|---|---|---|---|---|---|---|---|---|---|---|---|---|---|
| | | 3 | 20 | 0 | 0 | 0 | 11 | 0 | 9 | 45 | 2 | 0 | 18 | 90 | | |
| | | 4 | 20 | 0 | 0 | 0 | 17 | 0 | 3 | 15 | 2 | 0 | 18 | 90 | | |
| | Mean | | | | | 3.8 | | | | 31.3 | | | | 88.8 | | |
| 4. Formulation D | 9.8 kg/ha | 1 | 15 | 0 | 5 | 25 | 10 | 0 | 10 | 50 | 4 | 0 | 16 | 80 | | |
| | | 2 | 18 | 0 | 2 | 10 | 8 | 0 | 12 | 60 | 5 | 0 | 15 | 75 | | |
| | | 3 | 18 | 0 | 2 | 10 | 7 | 0 | 13 | 65 | 2 | 0 | 18 | 90 | | |
| | | 4 | 17 | 0 | 3 | 15 | 7 | 0 | 13 | 65 | 0 | 0 | 20 | 100 | | |
| | Mean | | | | | 15.0 | | | | 60.0 | | | | 86.3 | | |
| 5. WP Bti | 9.8 kg/ha | 1 | 0 | 0 | 20 | 100 | 0 | 0 | 20 | 100 | 0 | 0 | 20 | 100 | | |
| | | 2 | 0 | 0 | 20 | 100 | 0 | 0 | 20 | 100 | 0 | 0 | 20 | 100 | | |
| | | 3 | 0 | 0 | 20 | 100 | 0 | 0 | 20 | 100 | 0 | 0 | 20 | 100 | | |
| | | 4 | 0 | 0 | 20 | 100 | 0 | 0 | 20 | 100 | 0 | 0 | 20 | 100 | | |
| | Mean | | | | | 100.0 | | | | 100.0 | | | | 100.0 | | |
| 6. Vectobac | 7.0 kg/ha | 1 | 1 | 0 | 19 | 95 | 0 | 0 | 20 | 100 | 0 | 0 | 20 | 100 | | |
| | | 2 | 0 | 0 | 20 | 100 | 0 | 0 | 20 | 100 | 0 | 0 | 20 | 100 | | |
| | | 3 | 2 | 0 | 18 | 90 | 0 | 0 | 20 | 100 | 0 | 0 | 20 | 100 | | |
| | | 4 | 0 | 0 | 20 | 100 | 0 | 0 | 20 | 100 | 0 | 0 | 20 | 100 | | |
| | Mean | | | | | 96.3 | | | | 100.0 | | | | 100.0 | | |

A = Active,
KD = Knockdown,
D = Dead
M % = Mortality percentage.

TABLE 2

| Treatment | Rate mL/L | Rep. | 4 Hours | | | | 6 Hours | | | | 8 Hours | | | | 12 Hours | | | |
|---|---|---|---|---|---|---|---|---|---|---|---|---|---|---|---|---|---|---|
| | | | A | K | D | % M | A | K | D | % M | A | K | D | % M | A | K | D | % M |
| 1. Formulation A | 9.8 kg/ha | 1 | 20 | 0 | 0 | 0 | 19 | 1 | 0 | 5 | 19 | 0 | 1 | 5 | 17 | 0 | 3 | 15 |
| | | 2 | 20 | 0 | 0 | 0 | 19 | 1 | 0 | 5 | 19 | 0 | 1 | 5 | 16 | 0 | 4 | 20 |
| | | 3 | 19 | 1 | 0 | 5 | 17 | 3 | 0 | 15 | 17 | 1 | 2 | 15 | 14 | 0 | 6 | 30 |
| | | 4 | 20 | 0 | 0 | 0 | 19 | 1 | 0 | 5 | 19 | 0 | 1 | 5 | 17 | 2 | 1 | 15 |
| | Mean | | | | | 1.3 | | | | 7.5 | | | | 7.5 | | | | 20.0 |
| 2. Formulation B | 9.8 kg/ha | 1 | 20 | 0 | 0 | 0 | 17 | 3 | 0 | 15 | 8 | 0 | 12 | 60 | 9 | 0 | 11 | 55 |
| | | 2 | 19 | 1 | 0 | 5 | 13 | 7 | 0 | 35 | 7 | 0 | 13 | 65 | 4 | 0 | 16 | 80 |
| | | 3 | 19 | 1 | 0 | 5 | 13 | 7 | 0 | 35 | 9 | 0 | 11 | 55 | 8 | 0 | 12 | 60 |
| | | 4 | 20 | 0 | 0 | 0 | 17 | 3 | 0 | 15 | 11 | 0 | 9 | 45 | 9 | 0 | 11 | 55 |
| | Mean | | | | | 2.5 | | | | 25.0 | | | | 56.3 | | | | 62.5 |
| 3. Formulation C | 9.8 kg/ha | 1 | 20 | 0 | 0 | 0 | 20 | 0 | 0 | 0 | 20 | 0 | 0 | 0 | 17 | 0 | 3 | 15 |
| | | 2 | 20 | 0 | 0 | 0 | 20 | 0 | 0 | 0 | 20 | 0 | 0 | 0 | 19 | 0 | 1 | 5 |
| | | 3 | 20 | 0 | 0 | 0 | 20 | 0 | 0 | 0 | 20 | 0 | 0 | 0 | 20 | 0 | 0 | 0 |
| | | 4 | 20 | 0 | 0 | 0 | 20 | 0 | 0 | 0 | 20 | 0 | 0 | 0 | 20 | 0 | 0 | 0 |
| | Mean | | | | | 0.0 | | | | 0.0 | | | | 0.0 | | | | 5.0 |
| 4. Formulation D | 9.8 kg/ha | 1 | 20 | 0 | 0 | 0 | 19 | 1 | 0 | 5 | 17 | 0 | 3 | 15 | 12 | 0 | 8 | 40 |
| | | 2 | 20 | 0 | 0 | 0 | 19 | 1 | 0 | 5 | 19 | 0 | 1 | 5 | 17 | 0 | 3 | 15 |
| | | 3 | 20 | 0 | 0 | 0 | 20 | 0 | 0 | 0 | 19 | 0 | 1 | 5 | 17 | 0 | 3 | 15 |
| | | 4 | 20 | 0 | 0 | 0 | 19 | 1 | 0 | 5 | 18 | 0 | 2 | 10 | 16 | 0 | 4 | 20 |
| | Mean | | | | | 0.0 | | | | 3.8 | | | | 8.8 | | | | 22.5 |
| 5. WP Bti | 9.8 kg/ha | 1 | 0 | 20 | 0 | 100 | 0 | 0 | 20 | 100 | 0 | 0 | 20 | 100 | 0 | 0 | 20 | 100 |
| | | 2 | 0 | 20 | 0 | 100 | 0 | 0 | 20 | 100 | 0 | 0 | 20 | 100 | 0 | 0 | 20 | 100 |
| | | 3 | 0 | 20 | 0 | 100 | 0 | 0 | 20 | 100 | 0 | 0 | 20 | 100 | 0 | 0 | 20 | 100 |
| | | 4 | 0 | 20 | 0 | 100 | 0 | 0 | 20 | 100 | 0 | 0 | 20 | 100 | 0 | 0 | 20 | 100 |
| | Mean | | | | | 100.0 | | | | 100.0 | | | | 100.0 | | | | 100.0 |
| 6 Vectobac | 7.0 kg/ha | 1 | 15 | 5 | 0 | 25 | 6 | 14 | 0 | 70 | 3 | 0 | 17 | 85 | 1 | 0 | 19 | 95 |
| | | 2 | 15 | 5 | 0 | 25 | 7 | 13 | 0 | 65 | 6 | 0 | 14 | 70 | 2 | 0 | 18 | 90 |
| | | 3 | 14 | 6 | 0 | 30 | 4 | 16 | 0 | 80 | 2 | 0 | 18 | 90 | 0 | 0 | 20 | 100 |
| | | 4 | 14 | 6 | 0 | 30 | 3 | 17 | 0 | 85 | 3 | 0 | 17 | 85 | 0 | 0 | 20 | 100 |
| | Mean | | | | | 27.5 | | | | 75.0 | | | | 82.5 | | | | 96.3 |

| Treatment | Rate mL/L | Rep. | 24 Hrs | | | | 30 Hrs | | | | 48 Hrs | | | |
|---|---|---|---|---|---|---|---|---|---|---|---|---|---|---|
| | | | A | K | D | % M | A | K | D | % M | A | K | D | % M |
| 1. Formulation A | 9.8 kg/ha | 1 | 6 | 0 | 14 | 70 | 2 | 0 | 18 | 90 | 1 | 0 | 19 | 95 |
| | | 2 | 9 | 0 | 11 | 55 | 6 | 0 | 14 | 70 | 3 | 0 | 17 | 85 |
| | | 3 | 8 | 0 | 12 | 60 | 6 | 0 | 14 | 70 | 3 | 0 | 17 | 85 |
| | | 4 | 11 | 0 | 9 | 45 | 7 | 0 | 13 | 65 | 2 | 0 | 18 | 90 |
| | Mean | | | | | 57.5 | | | | 73.8 | | | | 88.8 |
| 2. Formulation B | 9.8 kg/ha | 1 | 2 | 0 | 18 | 90 | 1 | 0 | 19 | 95 | 1 | 0 | 19 | 95 |
| | | 2 | 0 | 0 | 20 | 100 | 0 | 0 | 20 | 100 | 0 | 0 | 20 | 100 |
| | | 3 | 1 | 0 | 19 | 95 | 0 | 0 | 20 | 100 | 0 | 0 | 20 | 100 |
| | | 4 | 2 | 0 | 18 | 90 | 0 | 0 | 20 | 100 | 0 | 0 | 20 | 100 |
| | Mean | | | | | 93.8 | | | | 98.8 | | | | 98.8 |
| 3. Formulation C | 9.8 kg/ha | 1 | 10 | 0 | 10 | 50 | 9 | 0 | 11 | 55 | 2 | 0 | 18 | 90 |
| | | 2 | 9 | 0 | 11 | 55 | 9 | 0 | 11 | 55 | 2 | 0 | 18 | 90 |
| | | 3 | 12 | 0 | 8 | 40 | 8 | 0 | 12 | 60 | 2 | 0 | 18 | 90 |

TABLE 2-continued

| | | | | | | | | | | | | | | | | |
|---|---|---|---|---|---|---|---|---|---|---|---|---|---|---|---|---|
| | | 4 | 15 | 0 | 5 | 25 | 8 | 0 | 12 | 60 | 1 | 0 | 19 | 95 | | |
| | Mean | | | | | 42.5 | | | | 57.5 | | | | 91.3 | | |
| 4. Formulation D | 9.8 kg/ha | 1 | 7 | 0 | 13 | 65 | 2 | 0 | 18 | 90 | 1 | 0 | 19 | 95 | | |
| | | 2 | 8 | 0 | 12 | 60 | 6 | 0 | 14 | 70 | 2 | 0 | 18 | 90 | | |
| | | 3 | 6 | 0 | 14 | 70 | 4 | 0 | 16 | 80 | 4 | 0 | 16 | 80 | | |
| | | 4 | 5 | 0 | 15 | 75 | 2 | 0 | 18 | 90 | 1 | 0 | 19 | 95 | | |
| | Mean | | | | | 67.5 | | | | 82.5 | | | | 90.0 | | |
| 5. WP Bti | 9.8 kg/ha | 1 | 0 | 0 | 20 | 100 | 0 | 0 | 20 | 100 | 0 | 0 | 20 | 100 | | |
| | | 2 | 0 | 0 | 20 | 100 | 0 | 0 | 20 | 100 | 0 | 0 | 20 | 100 | | |
| | | 3 | 0 | 0 | 20 | 100 | 0 | 0 | 20 | 100 | 0 | 0 | 20 | 100 | | |
| | | 4 | 0 | 0 | 20 | 100 | 0 | 0 | 20 | 100 | 0 | 0 | 20 | 100 | | |
| | Mean | | | | | 100.0 | | | | 100.0 | | | | 100.0 | | |
| 6 Vectobac | 7.0 kg/ha | 1 | 0 | 0 | 20 | 100 | 0 | 0 | 20 | 100 | 0 | 0 | 20 | 100 | | |
| | | 2 | 0 | 0 | 20 | 100 | 0 | 0 | 20 | 100 | 0 | 0 | 20 | 100 | | |
| | | 3 | 0 | 0 | 20 | 100 | 0 | 0 | 20 | 100 | 0 | 0 | 20 | 100 | | |
| | | 4 | 0 | 0 | 20 | 100 | 0 | 0 | 20 | 100 | 0 | 0 | 20 | 100 | | |
| | Mean | | | | | 100.0 | | | | 100.0 | | | | 100.0 | | |

TABLE 3

| Treatment | Rate mL/L | Rep. | 4 Hours | | | | 8 Hours | | | | 12 Hours | | | | 24 Hours | | | | 48 Hrs | | | |
|---|---|---|---|---|---|---|---|---|---|---|---|---|---|---|---|---|---|---|---|---|---|---|
| | | | A | K | D | % M | A | K | D | % M | A | K | D | % M | A | K | D | % M | A | K | D | % M |
| 1. E1 | 9.8 kg/ha | 1 | 20 | 0 | 0 | 0 | 18 | 0 | 2 | 10 | 13 | 0 | 7 | 35 | 5 | 0 | 15 | 75 | 1 | 0 | 19 | 95 |
| | | 2 | 20 | 0 | 0 | 0 | 16 | 0 | 4 | 20 | 14 | 0 | 6 | 30 | 3 | 0 | 17 | 85 | 2 | 0 | 18 | 90 |
| | | 3 | 20 | 0 | 0 | 0 | 15 | 0 | 5 | 25 | 13 | 0 | 7 | 35 | 10 | 0 | 10 | 50 | 3 | 0 | 17 | 85 |
| | | 4 | 20 | 0 | 0 | 0 | 12 | 0 | 8 | 40 | 11 | 0 | 9 | 45 | 5 | 0 | 15 | 75 | 0 | 0 | 20 | 100 |
| | Mean | | | | | 0.0 | | | | 23.8 | | | | 36.3 | | | | 71.3 | | | | 92.5 |
| 2. E2 | 9.8 kg/ha | 1 | 19 | 1 | 0 | 5 | 13 | 0 | 7 | 35 | 8 | 0 | 12 | 60 | 7 | 0 | 13 | 65 | 4 | 0 | 16 | 80 |
| | | 2 | 20 | 0 | 0 | 0 | 19 | 0 | 1 | 5 | 18 | 0 | 2 | 10 | 14 | 0 | 6 | 30 | 5 | 0 | 15 | 75 |
| | | 3 | 17 | 3 | 0 | 15 | 6 | 0 | 14 | 70 | 2 | 0 | 18 | 90 | 0 | 0 | 20 | 100 | 0 | 0 | 20 | 100 |
| | | 4 | 18 | 2 | 0 | 10 | 12 | 0 | 8 | 40 | 5 | 0 | 15 | 75 | 2 | 0 | 18 | 90 | 0 | 0 | 20 | 100 |
| | Mean | | | | | 7.5 | | | | 37.5 | | | | 58.8 | | | | 71.3 | | | | 88.8 |
| 3. E3 | 9.8 kg/ha | 1 | 19 | 1 | 0 | 5 | 3 | 0 | 17 | 85 | 3 | 0 | 17 | 85 | 1 | 0 | 19 | 95 | 1 | 0 | 19 | 95 |
| | | 2 | 20 | 0 | 0 | 0 | 4 | 0 | 16 | 80 | 3 | 0 | 17 | 85 | 0 | 0 | 20 | 100 | 0 | 0 | 20 | 100 |
| | | 3 | 18 | 2 | 0 | 10 | 7 | 0 | 13 | 65 | 6 | 0 | 14 | 70 | 2 | 0 | 18 | 90 | 0 | 0 | 20 | 100 |
| | | 4 | 18 | 2 | 0 | 10 | 8 | 0 | 12 | 60 | 6 | 0 | 14 | 70 | 3 | 0 | 17 | 85 | 2 | 0 | 18 | 90 |
| | Mean | | | | | 6.3 | | | | 72.5 | | | | 77.5 | | | | 92.5 | | | | 96.3 |
| 4. E4 | 9.8 kg/ha | 1 | 19 | 1 | 0 | 5 | 12 | 0 | 8 | 40 | 5 | 0 | 15 | 75 | 1 | 0 | 19 | 95 | 1 | 0 | 19 | 95 |
| | | 2 | 18 | 2 | 0 | 10 | 7 | 0 | 13 | 65 | 4 | 0 | 16 | 80 | 1 | 0 | 19 | 95 | 0 | 0 | 20 | 100 |
| | | 3 | 20 | 0 | 0 | 0 | 8 | 0 | 12 | 60 | 4 | 0 | 16 | 80 | 0 | 0 | 20 | 100 | 0 | 0 | 20 | 100 |
| | | 4 | 20 | 0 | 0 | 0 | 10 | 0 | 10 | 50 | 7 | 0 | 13 | 65 | 2 | 0 | 18 | 90 | 1 | 0 | 19 | 95 |
| | Mean | | | | | 3.8 | | | | 53.8 | | | | 75.0 | | | | 95.0 | | | | 97.5 |
| 5. WP Bti | 9.8 kg/ha | 1 | 0 | 20 | 0 | 100 | 0 | 0 | 20 | 100 | 0 | 0 | 20 | 100 | 0 | 0 | 20 | 100 | 0 | 0 | 20 | 100 |
| | | 2 | 0 | 20 | 0 | 100 | 0 | 0 | 20 | 100 | 0 | 0 | 20 | 100 | 0 | 0 | 20 | 100 | 0 | 0 | 20 | 100 |
| | | 3 | 0 | 20 | 0 | 100 | 0 | 0 | 20 | 100 | 0 | 0 | 20 | 100 | 0 | 0 | 20 | 100 | 0 | 0 | 20 | 100 |
| | | 4 | 0 | 20 | 0 | 100 | 0 | 0 | 20 | 100 | 0 | 0 | 20 | 100 | 0 | 0 | 20 | 100 | 0 | 0 | 20 | 100 |
| | Mean | | | | | 100.0 | | | | 100.0 | | | | 100.0 | | | | 100.0 | | | | 100.0 |
| 6 Vectobac | 7.0 kg/ha | 1 | 4 | 16 | 0 | 80 | 0 | 0 | 20 | 100 | 0 | 0 | 20 | 100 | 0 | 0 | 20 | 100 | 0 | 0 | 20 | 100 |
| | | 2 | 6 | 14 | 0 | 70 | 1 | 0 | 19 | 95 | 0 | 0 | 20 | 100 | 0 | 0 | 20 | 100 | 0 | 0 | 20 | 100 |
| | | 3 | 7 | 13 | 0 | 65 | 2 | 0 | 18 | 90 | 0 | 0 | 20 | 100 | 0 | 0 | 20 | 100 | 0 | 0 | 20 | 100 |
| | | 4 | 5 | 15 | 0 | 75 | 0 | 0 | 20 | 100 | 0 | 0 | 20 | 100 | 0 | 0 | 20 | 100 | 0 | 0 | 20 | 100 |
| | Mean | | | | | 72.5 | | | | 96.3 | | | | 100.0 | | | | 100.0 | | | | 100.0 |

A—Active,
K—Knockdown,
D—Dead
M %—Mortality percentage

Example 10

A composition was prepared in accordance with the invention was prepared as described in Table 4 to provide granules of composition shown in Table 5.

TABLE 4

| Step No. | Directions | Precautions |
|---|---|---|
| 1 | Inspect all equipment prior to commencing manufacture. Ensure all equipment is clean and ok to use. | |
| 2 | Place 205L stainless steel vessel with stirrer | Ensure safety |

TABLE 4-continued

| Step No. | Directions | Precautions |
|---|---|---|
| | and variable speed mixer on floor scales. | glasses and gloves are worn. |
| 3 | Record tare weight of vessel on batch sheet. | |
| 4 | Add 176 g of RD2910 oil and 5 g of Ecoteric T80 to vessel and turn on stirrer and mixer. | |
| 5 | Add 20 kg Bti wettable powder to vessel while mixing. Continue mixing until all Bti lumps have broken up and a uniform dispersion is formed. Record addition on batch sheet. Ensure dust extraction unit is turned on and suitable respirator is worn. | |

TABLE 4-continued

| Step No. | Directions | Precautions |
|---|---|---|
| 6 | Turn off mixer but ensure that stirrer remains turned on. Ensure stirrer remains turned on as this will prevent separation of the Bti in the RD2910 oil during the manufacturing process. | |
| 7 | To large cement-type mixer add 784 kg of bentonite. Turn on cement mixer. Record addition on batch sheet. | Ecoteric T80 may require heating prior to addition to vessel. Place at 60° C. overnight to reduce its viscosity. Record addition on batch sheet. |
| 8 | Gradually add the pre-mix of Bti in RD2910 oil to the bentonite while mixing. Record addition on batch sheet. | |
| 9 | Continue mixing for 10 minutes after the addition is complete. | |
| 10 | Gradually add 20 kg of Maltodextrin solution to the mixer. Mix for a further 10 minutes following addition. Record addition on batch sheet. | |
| 11 | Pass product through a sieve shaker to remove any large lumps and fines. Final particle size should be 1.0-2.0 mm. | |
| 12 | Obtain sample of batch and submit to QC laboratory for analysis. | |

TABLE 5

| Component | CAS No. | Chemical name | Constituent Standard | Conc. (g/kg) | Function |
|---|---|---|---|---|---|
| Bti WP (5000 IU/mg) | 2712-78-9 | *Bacillus thuringiensis* subspecies *Israelensis* active solids and solubles | Provided by Granular Products | 22.8 | Active Ingredient |
| RD2910 Oil | Proprietary | | MSDS | 176.0 | Carrier Oil |
| Ecoteric T80 | | | MSDS | 5.0 | Emulsifier |
| Maltodextrin solution (25 w/w %) | 9050-36-6 | Maltodextrin | MSDS | 20.0 | Film Former |
| Bentonite (1.0-2.0 mm) | 1302-78-9 | Montmorillonite | MSDS | 776.2 | Carrier |
| TOTAL | | | | 1000.0 | |

Example 11

Bti granules according to the invention were made according to the procedures of Formulation Example 10.

Fine material in the granule sample was removed by sieving the fines out through a 1 mm sieve.

300 g of sieved granules were added to 150 grams of attrition media (fustocone shaped plastic "fine cut" (aluminium oxide embedded abrasive) rolling media, each rolling media is fustocone of bottom diameter 7.7 mm and top diameter 5.7 mm and height of 7.7 mm) and added to a cylindrical rotation vessel (LORTONE 3A rotary tumbler (220 to 240 volts, 0.33 amps, 50/60 Hz) which was a 3 lbs rubber walled tumbler barrel, the internal dimensions of the tumbler barrel were 10.7 cm length and 9.7 cm diameter. The tumbler barrel was provided with six baffles which were 10 mm wide and 2 mm high.

The vessel was given a first rotation period at 53 rpm for 24 hours. After the completion of the first rotation period, the contents of the rotation vessel were sieved through a 1 mm sieve to recover attrition material (designated AM1) underneath the sieve. 8 grams of the sieved material (designated SM1) was separated and retained, and the balance of the sieved material was returned to the cylindrical rotation vessel.

The vessel was given a second rotation period at 53 rpm for 24 hours. After the completion of the second rotation period, the contents of the rotation vessel were sieved through a 1 mm sieve to recover attrition material (designated AM2) underneath the sieve. 8 grams of the sieved material (designated SM2) was separated and retained, and the balance of the sieved material was returned to the cylindrical rotation vessel.

The vessel was given a third rotation period at 53 rpm for 24 hours. After the completion of the third rotation period, the contents of the rotation vessel were sieved through a 1 mm sieve to recover attrition material (designated AM3) underneath the sieve. 8 grams of the sieved material (designated SM3) was separated and retained.

Samples SM1, SM2, SM3, AM1, AM2, and AM3 were sent to a test laboratory for protein determination (by the Kjeldahl method detailed in Table 6A). The results were as shown in Table 6B:

TABLE 6A

| Determination of Total Nitrogen by Kjeldahl | |
|---|---|
| Analysis Description | Determination of total nitrogen by Kjeldahl |
| Matrix/Matrices | Food and other organic matter |
| Reference Method(s) | AOAC 18$^{th}$ Ed. 981.10, 920.152, 990.03, 920.87 AS2300.1.2.1 |
| Limit of Reporting | Organic Matter - 0.02 g/100 g |
| NATA Accredited | Yes |
| Preparation and procedure | Preparation: Sample is homogenised by mortar and pestle and a sub sample (approx. 2 g) is accurately weight into a kjeldahl digestion tube. A digestion aid of potassium sulphate and a catalyst, copper sulphate is added to the sample, followed by 20 ml of concentrated sulphuric acid. The tube is slowly heated to 400° C. and then the temperature is maintained until the mixture in the tube is clear. The clear solution is digested for 1 hour and the tube allowed to cool. Determination: Once the tube has cooled 50 ml distilled water is added. The tube is placed in a Kjeltec distillation unit and the mixture is steam distilled into a beaker containing 50 ml of saturated boric acid solution. The distilled solution is titrated with standardised 0.1N sulphuric acid solution using a mixed indicator of bromcresol green and methyl red. Calculations: Total N (g/100 g) = 0.14 * (titre − blank)/sample mass or volume |
| Comments, limitations or known interferences | This is an internationally recognised reference method and provides comparability with measurements made worldwide. |
| Equipment used | Digestion Tubes, beakers and other glassware Balance Kjeldahl digestion block - 20 place/up to 440 c Kjeltec (Kjeldahl) steam distillation unit Auto-titration system |

TABLE 6A-continued

Determination of Total Nitrogen by Kjeldahl

| | |
|---|---|
| QA Protocols per batch | Reference skim milk powder Control with each batch. Tyrosine recovery with each batch. Minimum of 1 duplicate analysis per batch - maximum batch size is 16 samples. |
| Mass of Sample required | 10 g per sample, however more sample would be required for QA. |

TABLE 6B

| Sample | Protein (as total nitrogen g/100 g) |
|---|---|
| SM1 | 0.07 |
| SM2 | 0.08 |
| SM3 | 0.06 |
| AM1 | 0.10 |
| AM2 | 0.13 |
| AM3 | 0.15 |
| Bti wettable powder dry sample | 2.6 |

Attrition material in all cases contained significantly more protein than sieved material, which shows that the outer shell of the Bti granules was richer in Bti than the inner region.

Note that when protein assays were conducted on core granules (before loading with Bti), the protein reading was "not detectable".

Example 12

A granular composition in accordance with the invention comprising a relatively high load of the larvicide Btl was prepared using the process of Example 10 with the composition described in Table 7.

TABLE 7

| Component | CAS No. | Chemical name | Conc. (g/kg) | Function |
|---|---|---|---|---|
| Bti WP (5000 IU/mg) | 2712-78-9 | Bacillus thuringiensis subspecies Israelensis active solids and solubles | 45.6 | Active Ingredient |
| RD2910 Oil | Proprietary | | 176 | Carrier Oil |
| Ecoteric T80 | | | 5 | Emulsifier |
| Maltodextrin solution (25 w/w %) | 9050-36-6 | Malto-dextrin | 20 | Binder |
| Bentonite (1.0-2.0 mm) | 1302-78-9 | Montmorillonite | 753.4 | Carrier |
| TOTAL | | | 1000 | |

ECOTERIC T80 is polyoxyethylene(20)sorbitan monooleate
Comments: Granules were free flowing and appear dry

Example 13

A further granular larvicidal composition in accordance with the invention was prepared in accordance with the process of Example 10 with the components and amounts shown in Table 8.

TABLE 8

| Component | CAS No. | Chemical name | Conc. (g/kg) | Function |
|---|---|---|---|---|
| Bti WP (5000 IU/mg) | 2712-78-9 | Bacillus thuringiensis subspecies Israelensis active solids and solubles | 45.6 | Active Ingredient |
| RD2910 Oil | Proprietary | | 176 | Carrier Oil |
| Ecoteric T80 | | | 5 | Emulsifier |
| Maltodextrin solution (40 w/w %) | 9050-36-6 | Malto-dextrin | 20 | Binder |
| Bentonite (1.0-2.0 mm) | 1302-78-9 | Montmorillonite | 730.7 | Carrier |
| TOTAL | | | 1000 | |

Comments: Granules were free flowing and appear dry

Example 14

This Example relates to a field trial designed to test the granules of Example 10 in freshwater and saltwater situations. The trial was located in Darwin, Australia and was carried out over two days in January. The granules were added to temporary pools at a rate of 1 g/m$^2$. Results were recorded at 24 hrs and 48 hrs after application.

The amount of mosquito larvae present was calculated using a larval dipper, 10-15 dips were taken at each site and the number of mosquitoes was recorded as an average "per dip".

Results showed that the granules were successful in the control of mosquitoes, with results at 48 hours or longer showing the most significant.

After 48 hours, of those found, larvae ranged from $1^{st}$-$4^{th}$ instar. $1^{st}$ instar can be expected after 48 hours in this case, as larvae hatch within 12 hours of a rain event and this population was expected to be unaffected by the treatment at such an early stage. During this field trial 24 mls of rain occurred between 36 and 48 hours.

Treatment with the granules caused control of immature mosquito within 48 hours, it would be important to test residual control over a greater period of time.

The results of the trial are shown in Table 9.

TABLE 9

DARWIN FIELD TRIAL - JANUARY 2015

| SITE | LOCATION | AREA | GRANULES (g) | Abundance (per dip) | OBSERVATIONS | RESULTS- 24 HOURS | RESULTS- 24 HOURS |
|---|---|---|---|---|---|---|---|
| 1 | Lee Point 12° 19'48.3" S 130° 53'44.7" E | 25 × 10 m | 250 g | 30 p.d Ades Vigilex 2nd-3rd Instar | Saltwater Tadpoles present 10:20 am, 31.7° C. Avg. wind speed-4.5 km/h r.h. 77.5% | Average of 11 p.d 63% kill | Average of <1 p.d 97% kill |

TABLE 9-continued

DARWIN FIELD TRIAL - JANUARY 2015

| SITE | LOCATION | AREA | GRANULES (g) | Abundance (per dip) | OBSERVATIONS | RESULTS- 24 HOURS | RESULTS- 24 HOURS |
|---|---|---|---|---|---|---|---|
| 2 | Vesty Lake 12° 25'52.9" S 130° 50'07.1" E | 8 × 10 m | 80 g | 15 p.d Culex 2-3rd Instar | Fresh Water 10:49 am, 32° C. Avg. wind speed- 5.7 km/h r.h 76.4% | Average of 1.5 p.d. 90% kill | Average of 1 p.d. 93% kill |
| 3 | Vesty Lake 12° 25'52.9" S 130° 50'07.1" E | 6 × 10 m | 70 g | 5 p.d. Culex and Ades Vigilex present 2nd, 3rd and 4th Instar | Fresh Water 10:49 am, 32° C. Avg. wind speed- 5.7 km/h r.h. 76.4% | Average of 1 p.d. 80% kill | Average of 1 2-3rd instar p.d. 80% kill Average of 10 1st instar p.d.* |
| 4 | Vestys Lake 12° 25'58.9" S 130° 50'12.3" E | 15 × 10 m | 150 g | 5. p.d. Culex 2nd-3rd Instar | Fresh Water 10:49 am, 32° C. Avg. wind speed- 5.7 km/h r.h. 76.4% | Dried up since application, unable to record | 0 p.d. |
| 5 | Waste Depot 12° 23'13.1"" S 130° 55'35.6"" E | 1 × 15 m | 15 g | 5 p.d. Culex 2nd-3rd Instar | Fresh Water, High nutrient 11:31 am, 31.1° C. Avg. wind speed-6 km/h r.h 75.5% | Average of 4. p.d | 0 p.d. 100% kill |
| 6 | Waste Depot 12° 23'13.1"" S 130° 55'35.6"" E | 23 × 21 m | 483 g | 30 p.d Ades Vigilex and Culex 2nd, 3rd and 4th Instar | Fresh Water, High nutrient 11:31 am, 31.1° C. Avg. wind speed-6 km/h r.h 75.5% | Average of 4 p.d | Average of <1 p.d 98% kill | r.h.—relative humidity
*A number of first instar can be expected after 48 hours of application as they hatch 12 hours after a rain event. A rain event occurred at 36 hours after application.

Example 15

The granules in accordance with the invention (200 ITU and 100 ITU) and reference "Vectobac" granules are applied from aircraft shown in Table 10 and may achieve the application parameters shown in Table 10.

TABLE 10

| Aircraft Type | | Granules[1] 200 ITU | #Granules[2] 100 ITU | Vectobac G |
|---|---|---|---|---|
| #Bell 206 (110 KPH) | Swath | 12 m | 12 m | 8 m |
| | Area per minute | 2.6 Ha/min | 2.6 Ha/min | 1.5 Ha/min |
| | Ha treated/ hopper load | 102 Ha | 51 Ha | 29 Ha |
| #Bell 47 (80 KPH) | Swath | 12 | 12 | 8 |
| | Area per minute | 1.6 Ha/min | 1.6 Ha/min | 1.1 Ha/min |
| | Ha treated/ hopper load | 72 Ha | 36 Ha | 29 Ha |
| #R 44/66 (95 KPH) | Swath | 12 | 12 | 8 |
| | Area per minute | 1.9 Ha/min | 1.9 Ha/min | 1.3 Ha/min |
| | Ha treated/ hopper load | 62 Ha | 31 Ha | 28 Ha |
| #Bell 204/ 205 (150 KPH) | Swath | 15 | 15 | 10 |
| | Area per minute | 3.75 Ha/Min | 3.75 Ha/Min | 2.5 Ha/Min |
| | Ha treated/ hopper load | 246 Ha | 123 | 114 |

*Fixed wing aircraft
helicopter
[1]Granules 200 ITU are the granules according to Example 12
[2]Granules 100 ITU are the granules according to Example 10

The invention claimed is:

1. An insecticidal granular composition for broadcasting of the granular composition onto a body of water on which insects are to be controlled comprising:
   a granular carrier of size in range of from 1 to 4 mm, wherein the granular carrier comprises a clay selected from the group consisting of attapulgite, bentonite or a mixture thereof and is present in the insecticidal granular composition in an amount of 60% to 95% w/w;
   a composition absorbed into the granular carrier comprising a bacterially derived larvicidal active agent in an amount of from $3 \times 10^6$ to $60 \times 10^6$ ITU per 100 g of granules and 1% to 30% w/w of the granular composition of a non-aqueous liquid having a density less than 1 g per cubic centimeter, wherein the larvicidal active agent is *Bacillus thuringiensis*, *Bacillus sphaericus* or a mixture thereof and wherein the non-aqueous liquid comprises a surfactant; and
   water-dispersible polymer binder forming a coating on the granules, wherein the water dispersible polymer binder is selected from the group consisting of carbohydrate, protein, lipid synthetic polymer, glycolipid, glycoprotein, lipoprotein, lignin, lignin derivative selected from lignosulfonate salts, and combinations thereof, wherein the water dispersible polymer binder is present in an amount of up to 3% w/w of the granular composition;
   wherein the insecticidal granular composition has an average individual granule density greater than 1, a packing density of at least 0.7 g per cubic centimeter and is adapted to sink in the body of water.

2. An insecticidal granular composition according to claim 1, wherein the granular carrier has a sorption capacity for the non-aqueous liquid of at least 5% by weight.

3. An insecticidal granular composition according to claim 1 comprising;
   from 3% to 20% w/w non-aqueous liquid; and
   from $7.5 \times 10^6$ to $20 \times 10^6$ ITU per 100 g granules.

4. An insecticidal granular composition according to claim 1 wherein the water dispersible polymer binder is a polysaccharide or modified polysaccharide.

5. An insecticidal granular composition according to claim 1, wherein the water dispersible polymer binder is present in an amount of from 0.2% to 2% by weight.

6. An insecticidal granular composition according to claim 1, wherein the surfactant is present in an amount of 0.3% to 5% w/w of the composition.

7. An insecticidal granular composition according to claim 1, wherein the concentration of the larvicidal active agent is greater in an outer portion of the individual granules than in the core of the granules.

8. An insecticidal granular composition according to claim 1, wherein the non-aqueous liquid has a density in the range of from 0.75 to 0.99 g/ml.

9. An insecticidal granular composition according to claim 1, wherein the non-aqueous liquid comprises an ethoxylated fatty alcohol.

10. An insecticidal granular composition according to claim 1, wherein the ratio of larvicidal active agent to non-aqueous liquid is in the range of from 8% to 50% by weight.

11. An insecticidal granular composition according to claim 1, wherein the granular carrier is non-agglomerated.

12. An insecticidal granular composition according to claim 1, wherein the granular carrier disintegrates in water within a period of no more than 60 minutes.

13. An insecticidal granular composition according to claim 1, having a packing density of at least 0.8 g per cubic centimeter.

14. A process for preparation of an insecticidal granular composition according to claim 1 for broadcasting onto a body of water, comprising:

providing a granular carrier of size in the range of from 1 to 4 mm, wherein the granular carrier comprises a clay selected from the group consisting of attapulgite, bentonite or a mixture thereof and is in an amount of 60% to 95% w/w of the insecticidal qranular composition; and mixing the granular carrier with a suspension of bacterially derived larvicidal active agent in an amount of $3 \times 10^6$ to $60 \times 10^6$ ITU per 100 g of insecticidal granular composition in 1% to 30% w/w of the insecticidal qranular composition of a non-aqueous liquid to absorb the suspension into the qranular carrier, wherein the larvicidal active agent is *Bacillus thuringiensis, Bacillus sphaericus* or a mixture thereof and wherein the non-aqueous liquid comprises a surfactant;

subsequently adding a binder to the granules, wherein the binder is selected from the group consisting of carbohydrates, protein, lipid synthetic polymer, glycolipid, glycoprotein, lipoprotein, lignin, lignin derivative selected from lignosulfornate salts, and combinations thereof, wherein the binder is present in an amount of up to 3% w/w of the granular composition;

wherein the non-aqueous liquid has a density less than 1 g per cubic centimeter and the insecticidal granular composition has an average individual granule density greater than 1 g per cubic centimeter, a packing density of 0.7 g per centimeter and is adapted to sink in the body of water.

15. A process according claim 14, wherein the granular carrier and suspension are mixed in a rotating drum mixer.

* * * * *

UNITED STATES PATENT AND TRADEMARK OFFICE
CERTIFICATE OF CORRECTION

PATENT NO. : 10,226,049 B2
APPLICATION NO. : 15/114622
DATED : March 12, 2019
INVENTOR(S) : Graham Barrett et al.

It is certified that error appears in the above-identified patent and that said Letters Patent is hereby corrected as shown below:

In the Claims

Claim 3, Column 24, Line 62, delete "comprising;" and insert --comprising:--.
Claim 14, Column 26, Line 5, delete "qranular" and insert --granular--.
Claim 14, Column 26, Line 11, delete "qranular" and insert --granular--.
Claim 14, Column 26, Line 12, delete "qranular" and insert --granular--.

Signed and Sealed this
Ninth Day of July, 2019

Andrei Iancu
*Director of the United States Patent and Trademark Office*